United States Patent [19]
Songer et al.

[11] Patent Number: 5,741,260
[45] Date of Patent: Apr. 21, 1998

[54] CABLE SYSTEM FOR BONE SECURANCE

[75] Inventors: Matthew N. Songer, Marquette; Francis J. Korhonen, Nequanee, both of Mich.

[73] Assignee: Pioneer Laboratories, Inc., Marquette, Mich.

[21] Appl. No.: 803,503

[22] Filed: Feb. 20, 1997

Related U.S. Application Data

[62] Division of Ser. No. 569,707, Dec. 8, 1995, which is a division of Ser. No. 201,614, Feb. 24, 1994, Pat. No. 5,536,270.

[51] Int. Cl.⁶ .................................................. A61B 17/82
[52] U.S. Cl. .......................... 606/74; 606/103; 140/105; 220/309.1
[58] Field of Search .................. 606/74, 72, 60, 606/103, 61, 86, 135, 151, 139, 144, 148, 232; 140/105, 106; 220/309.1

[56] References Cited

U.S. PATENT DOCUMENTS

| | | | |
|---|---|---|---|
| 2,049,361 | 7/1936 | Ericsson | 606/74 |
| 3,035,583 | 5/1962 | Hirsch et al. | |
| 3,507,270 | 4/1970 | Ferrier | 606/74 |
| 4,054,144 | 10/1977 | Hoffman et al. | 606/74 |
| 4,691,704 | 9/1987 | Wadsworth | 606/74 |
| 5,116,340 | 5/1992 | Songer et al. | 606/103 |
| 5,133,738 | 7/1992 | Korthoff et al. | |
| 5,236,434 | 8/1993 | Callicrate | 606/135 |
| 5,374,268 | 12/1994 | Sander . | |
| 5,417,690 | 5/1995 | Sennett et al. | |
| 5,486,197 | 1/1996 | Le et al. | |
| 5,536,270 | 7/1996 | Songer et al. | 606/74 |

OTHER PUBLICATIONS

Document by Richards entitled: Orthopaedic Cable Tensioner and Titanium Cable, 5 pages, Dec., 1988 (Author Unknown).
Brochure –Codman –Sof'wire Cable System –6 pages, Jun., 1992 (Author Unknown).
Document entitled: Pilling–Wolvek Sternal Approximator and Fixation System, 1 page (Date and Author Unknown).
Document by Acumed, Inc., entitled: Osteo–Clage, Cerclage Cable System, 4 pages, Jul., 1992 (Author Unknown).
Document by Howmedica (UK) Limited, entitled: The Trochanter Cable Grip System, 6 pages, Jan., 1983 by Desmond M. Dall et al.
Document by Howmedica entitled: The Dall–Miles Trochanter Cable Grip System, 13 pages, May, 1986 (Author Unknown).
Document by Howmedica entitled: Dall–Miles Cable Grip System, 2 pages, Jun., 1993, (Author Unknown).

Primary Examiner—Guy V. Tucker
Attorney, Agent, or Firm—Gerstman, Ellis & McMillin, Ltd.

[57] ABSTRACT

Surgical crimping pliers have operating handles and connected, opposed jaws. The jaws define opposed recesses for carrying and crimping a tubular crimp member, which is preferably of oval configuration for carrying a plurality of multistrand cable sections so that, upon crimping, the cable sections are secured together. A capstan is carried on one of the handles for winding a plurality of cable portions so that tension may be placed on both ends of a cable loop array wound about a bone structure, to provide a predetermined, quantitative tension. Then the cable sections within the crimp are secured together by collapse of the crimp. A multistrand cable is preferably used, which exhibits great advantage over single strand wire, and which carries surgical needles of differing type secured to each end thereof.

6 Claims, 4 Drawing Sheets

CABLE SYSTEM FOR BONE SECURANCE

This is a division of application Ser. No. 08/569,707, filed Dec. 8, 1995, pending which is a division of application Ser. No. 08/201,614, filed Feb. 24, 1994, now U.S. Pat. No 5,536,270.

BACKGROUND OF THE INVENTION

This present invention is a surgical cable system for securance of the sternum following coronary bypass surgery, as well as for other desired bone securance uses.

In Songer, et al. U.S. Pat. No. 5,116,340 a surgical securance apparatus is disclosed in which a loop of surgical cable may be formed with crimping pliers having a capstan on one of the handles, for winding the surgical cable to provide crimping under a desired and predetermined level of tension. While this system is being successfully used in various clinical applications, there are certain desired clinical uses of crimped surgical cables for which the system of the above-cited patent is not optimum. Thus, by this invention, improvements are provided in surgical cables and the handling thereof to facilitate additional surgical procedures, above and beyond what was possible in the prior art.

In the prior art, surgery in and adjacent to the heart generally requires the central opening of the sternum to provide the surgeon with access. After the operation, the sternum is closed, typically with monofilament wire of about twenty gauge. Such wire is subject to breakage. Additionally, monofilament wire can not be tightened to a degree that is often desirable since, as wires are tightened, the wire is stressed so that further tightening may fracture the wire. However, if the wire tension against the sternum is undesirably low, the sternum is not rigidly fixed. This results in more post-operative pain than in the case with patients which have a rigidly fixed sternum due to better securance.

For this and other reasons, the monofilament wire securance of the sternum in accordance with the prior art has disadvantages and shortcomings.

DESCRIPTION OF THE INVENTION

In this invention, crimping pliers are provided which comprise a pair of operating handles in connected, opposed jaws. The jaws define opposed recesses for carrying and crimping a tubular crimp member by manual pressure on the operating handles. A capstan is carried on one of the handles for winding a pair of cable portions which respectively pass through a tubular crimp member carried in the jaws. The capstan also comprises a rotating handle for effecting the winding of the pair of cable portions.

The crimping pliers of this invention may have a capstan which comprises a pair of separate, rotatable drums for respectively receiving wound cable portions of the cable pair, the drums being each simultaneously rotated by the handle.

It is also preferred for the jaws of the crimping pliers of this invention to carry at least one laterally mounted wheel member, positioned to peripherally receive a portion of a cable extending laterally from the crimp member in the jaws, to cause the portion of the cable to peripherally bend around the wheel to extend longitudinally along the pliers, to engage the capstan. Thus, this approximately right angle bend of the cable makes possible the effective tightening of the cable without frictional binding or imposing a sharp angle on the cable, as the cable passes through a crimp member which is transversely positioned in an elongated chamber of the crimping pliers jaws.

Preferably, a pair of such wheel members are provided, each carried on an opposite side of the jaws, and each wheel member respectively so engaging one of the pair of cable portions.

Typically, the cable portions may be sections of the same cable, so that both ends of the same cable may be tensioned by the crimping pliers of this invention, to provide desired tension in a surgical cable winding supporting bones of the patient. For example, cable windings where the sternum is reclosed is illustrated in one of the drawings below. Then, crimping of the crimp member about the two cable sections of each cable winding can secure a central portion of the cable together into a closed loop winding, followed by cutting away both cable end portions which are outside of the crimp.

Opposed recesses defined in the pliers jaws preferably together define the elongated chamber of the jaws when the jaws are closed, which chamber extends in a direction normal to the axis of the pliers and to the direction of the jaw opening and closing in its longest chamber dimension.

Preferably, the crimp which is placed into the jaws of the pliers and collapsed therein is tubular. The crimp is preferably of oval cross-section, having a major and a minor oval axis. The major axis of the cross-section is preferably positioned in the direction of jaw opening and closing. Thus, when the crimp contains two separate lengths of cable in side-by-side relation, as facilitated by the oval section, collapsing of the crimp causes the crimp at first to typically assume a cross-section which is more circular, followed by collapse into a configuration where the cables are firmly retained together.

It is also preferred for the above crimp to define an outwardly projecting flange about each end thereof. The respective flanges are preferably frustoconical in shape, having a side angle to the tubular crimp longitudinal axis of about thirty to sixty degrees.

The surgical cable of this invention is preferably of multistrand type, having about 30 to 100 wound strands. Prior to emplacement in a patient, it may define a pair of opposed ends, each cable end being permanently secured to a surgical needle. Preferably, each of the surgical needles are of different types so that the cable can be easily implanted through differing types of tissue, with one needle being more effective for some types of implantation of the cable and the other needle being effective for other types. Specifically, one of the surgical needles may define a generally conical end terminating in a point, while the other of the surgical needles defines a point and a lateral cutting edge.

DESCRIPTION OF THE DRAWINGS

Referring to the drawings.

DESCRIPTION OF SPECIFIC EMBODIMENTS

Figure 1:
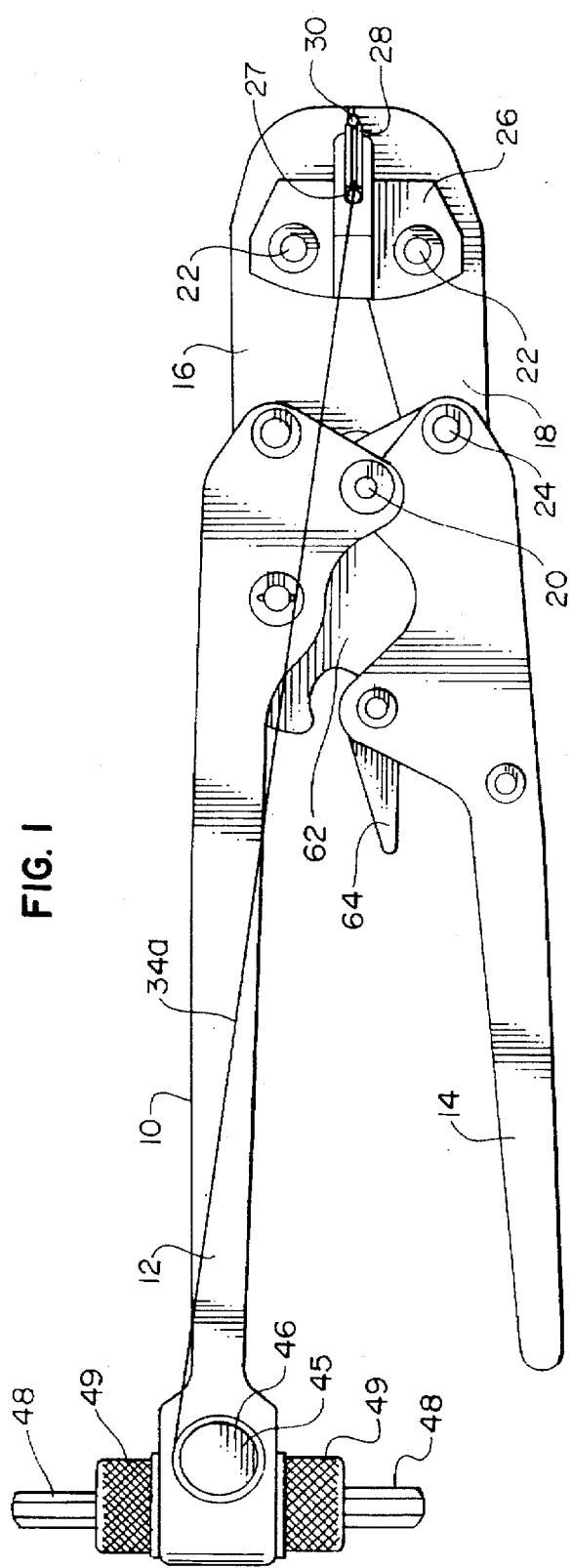
FIG. 1 is a plan view of surgical pliers made in accordance with this invention.
Figure 2:
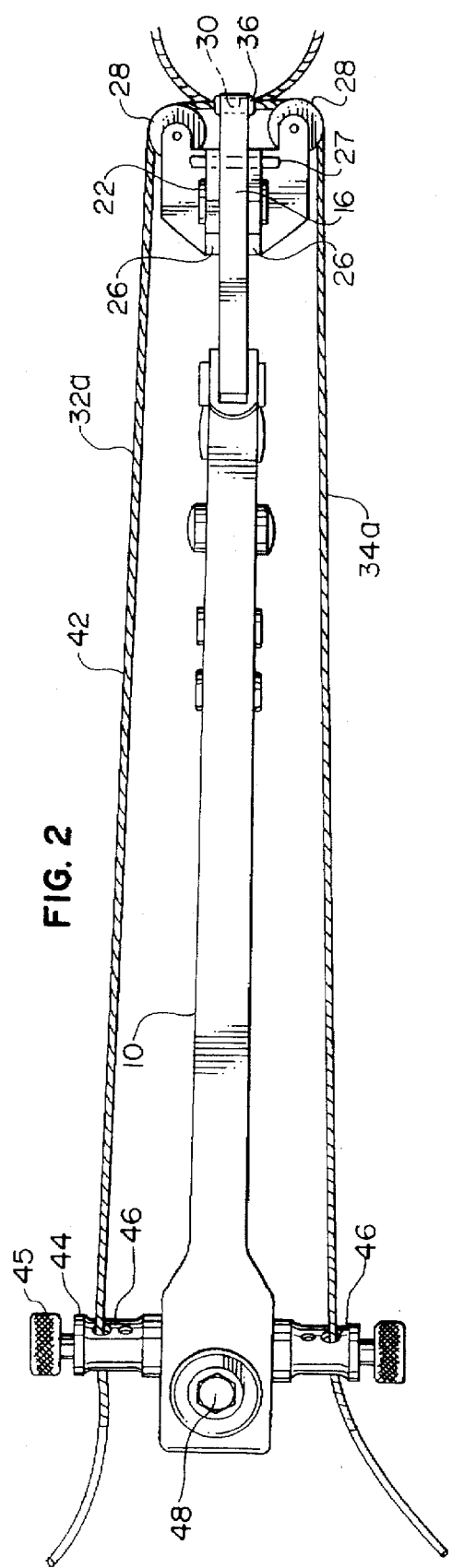
FIG. 2 is an elevational view of the surgical pliers of FIG. 1.

Referring to FIGS. 1 and 2, ratchet type crimping pliers 10 are shown, comprising a pair of operating handles 12, 14, and connected, opposed crimping jaws 16, 18. The mechanism of crimping pliers 10 may be substantially that of the prior art except as otherwise indicated herein, where the rotating of handles 12, 14 about pivot 20 causes pivoting of jaws 16, 18 about respective pairs of pivots 22, 24. Pivots 22 extend through a pair of metal straps 26 for the pivoting support of jaws 16, 18. Pin 27 is provided for load equalizing between straps 26, and fits loosely between jaws 16, 18.

Figure 3:
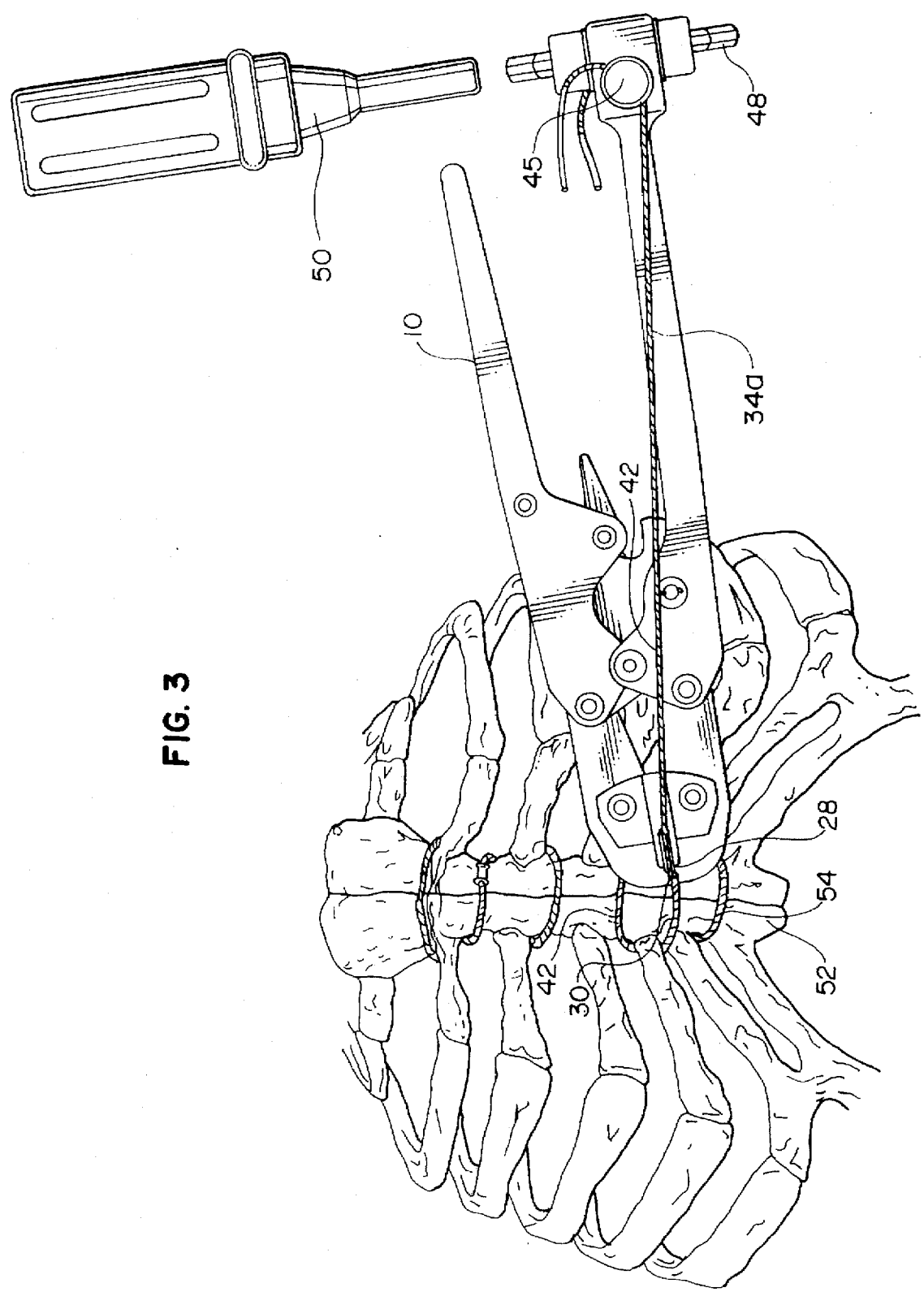
FIG. 3 is a perspective view showing the surgical pliers of FIGS. 1 and 2 in use with a torque wrench, securing and tensioning a cable which is wound around the sternum of a patient to reclose the sternum after surgery.
Figure 4:
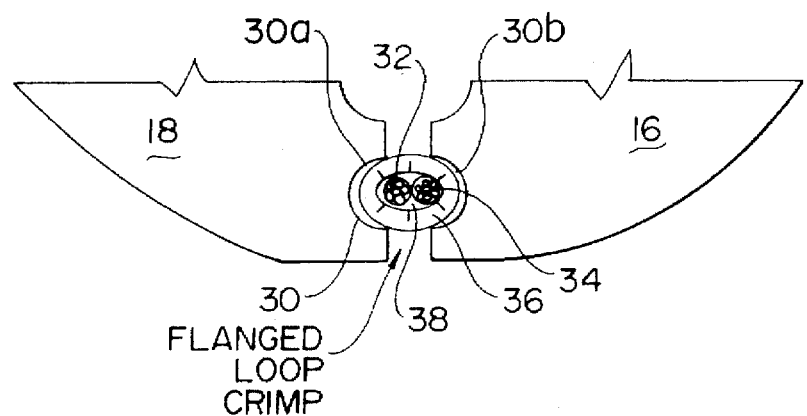
FIG. 4 is an enlarged, fragmentary, elevational view of the jaws of the pliers of FIG. 3 and the crimp of this invention, with the cables passing through the crimp being shown in section.
Figure 5:
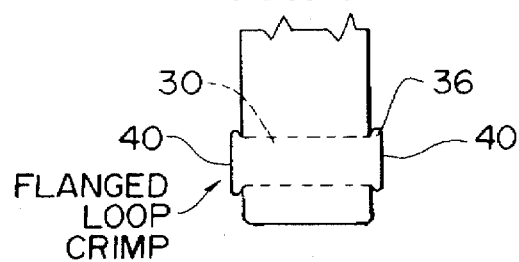
FIG. 5. is a fragmentary, sectional view taken along A—A of FIG. 4.

Also, each of metal straps 26 carry a laterally mounted wheel 28, each of which has a periphery positioned in lateral or transverse manner to receive a cable portion passing through transversely elongated chamber 30 which is defined by opposed recesses in the respective jaws 16, 18, being more particularly illustrated in FIGS. 3-5. In FIG. 4, cable portions 32, 34 are shown to be positioned within elongated chamber 30 as defined by recesses 30a and 30b. Cable portions 32, 34 are surrounded by tubular metal crimp 36, which is retained within elongated chamber 30.

As shown, tubular metal crimp may preferably have an oval cross section both in its outer periphery and its bore 38, with the recesses 30a, 30b being proportioned to receive crimp 36 with its oval cross section major axis extending in the direction of jaw opening and closing as shown in FIG. 4. Thus, upon closing of the jaws (the jaws of FIG. 4 being in an incompletely closed position) crimp 36 is collapsed first toward a bore 38 of more circular configuration, followed by a collapsed configuration that firmly retains cable portions 32, 34 together in bound relation.

Also, tubular crimp 36 is shown to have an outwardly projecting flange 40 on each end thereof, which may be a flaring end at an angle of about 45° to the major access of tubular crimp 36, or any other desired flange. One main purpose of each flange 40 is to facilitate introduction of cables in each direction through the crimp. Also, flanges 40 help retain crimp 36 in the position within elongated chamber 30 defined between jaws 16, 18, so that the crimp does not easily fall out of its position as cable portions are being threaded through it, prior to the crimping process exerted on crimp 36 by the pliers 10.

Cable portions 32, 34 comprise separate sections of typically a single cable 42, which has end sections 32a, 34a, each of which extend from their respective cable portions 32, 34 within crimp 36 laterally outwardly about a respective wheel 28 and then rearwardly along the pliers handle 12 to a capstan member 44 (FIG. 2). Capstan member 44 comprises a shaft which carries a pair of rotary drums 46 on opposite sides of handle 12, with shaft 45 extending completely through handle 12. Shaft 48 also extends through the end of handle 12 as shown to serve as a single, rotating handle for controlling the winding of drums 46 through typically a self-locking worm gear arrangement with shaft 45. Either shaft 45 or shaft 48 may comprise the worm gear, with the other shaft carrying an appropriate rotary gear for engaging with the worm, in the manner similar to that specifically illustrated in Songer U.S. Pat. No. 5,116,340, the disclosures of which are incorporated by reference herein.

As shown in FIG. 3, a torque wrench 50 may be provided to engage shaft 48, and rotated to cause corresponding rotation of shaft 45 and both drums 46. Thus the respective cable ends 32a, 34a of cable 42 may be simultaneously tightened.

In FIG. 3, cable 42 is shown to be wrapped about the sternum 52 of a patient which has been split for surgery within the rib cage. Then, cable 42 is wrapped in a desired, surgical manner about the sternum. Both end portions 32a, 34a are tightened in the manner illustrated by rotation of the torque wrench to wrap the ends of cable 42 about both drums 46 in simultaneous manner. Thus, the wrapping of a central cable portion about the sternum 52 is accomplished until a desired tightness is reached, which may be controlled by an appropriate setting on the torque wrench 50. Then, pliers 10 may be activated to crush crimp 36, to hold cable winding 54 in a permanent, closed position about the sternum. Following this, the end portions 32a, 34a of the cable outside of crimp 36 may be cut and removed, resulting in a finished, surgical cable loop windings of a type similar to that shown in FIG. 8.

Figure 8:
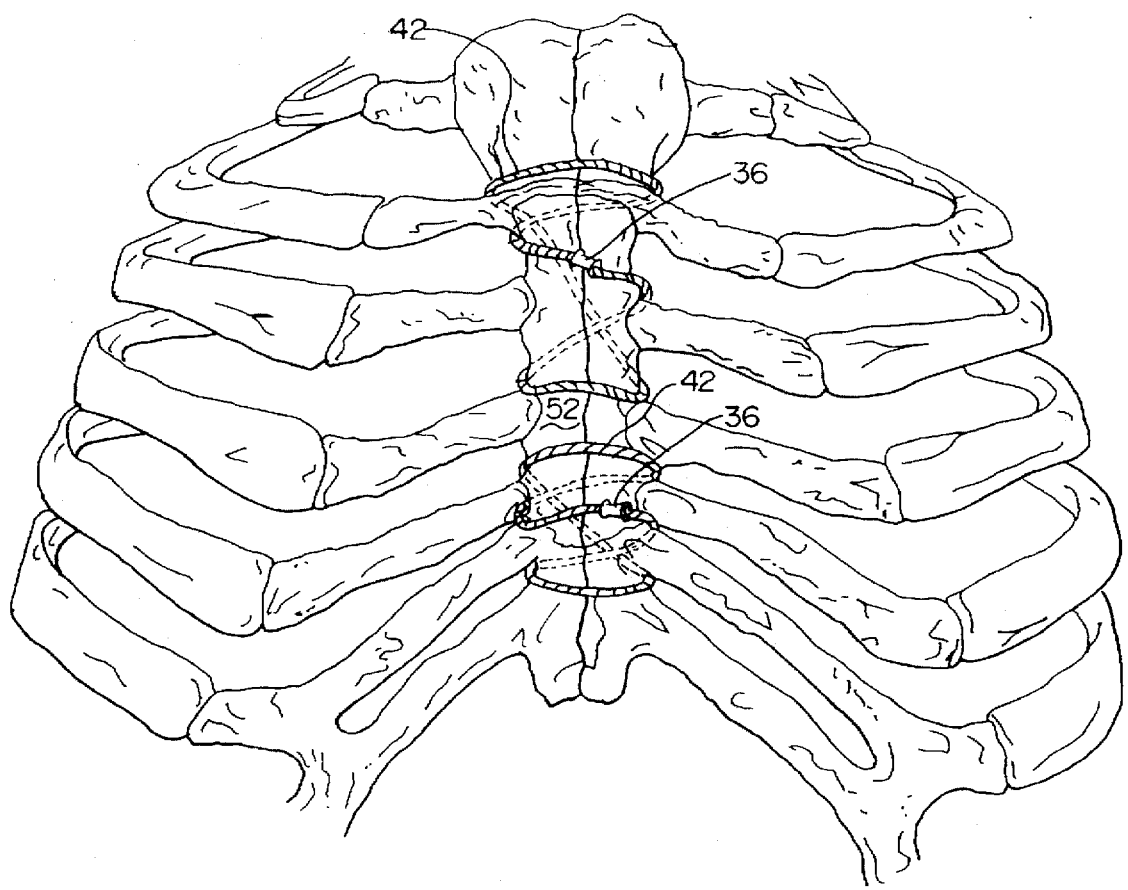
FIG. 8 is a plan view of the sternum of a patient, showing one way that surgical cables may be implanted to close the sternum in accordance with this invention.

In FIG. 8, a closure of the sternum is seen, using a pair of cable windings which may be simultaneously applied with a pair of pliers 10, or sequentially applied with the same set of pliers. The cutting of the cable sections outside of crimp 36 has been accomplished, leaving each cable portion 42 secured together in a loop form which is convoluted about the sternum 52 in a manner deemed best by the surgeon.

Figure 6:
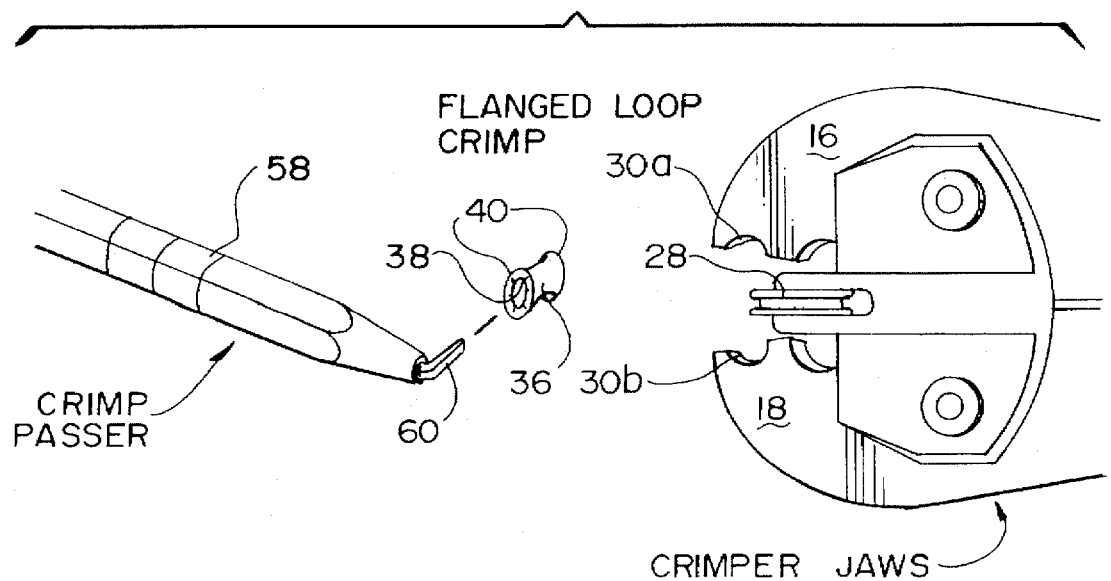
FIG. 6 is a fragmentary perspective view, showing the loading of a crimp into the opposed recesses of the jaws of the pliers of the previous figures.

FIG. 6 shows how the crimp 36 of this invention can be placed into the elongated chamber defined between the recesses 30a, 30b in the respective jaws. The view of FIG. 6 is greatly magnified. Crimp passer 58 comprises a handle which defines at one end a small projection 60 which is at a 90° angle to the rest of the crimp passer 58. Projection 60, in turn, fits into the oval bore 38 of crimp 36, to permit the crimp to be placed into one of the recesses 30b with its long oval axis pointing in the direction of jaw closing. Then, crimp passer 58 may be withdrawn, and the end flanges 40 of the crimp assist holding the crimp in position until the jaws are closed.

Pliers 10 may have a conventional ratchet assembly 62, which prevents opening of the pliers until the crimp is completely closed. However, a conventional release lever 64 is provided for release of the ratchet.

Figure 7:
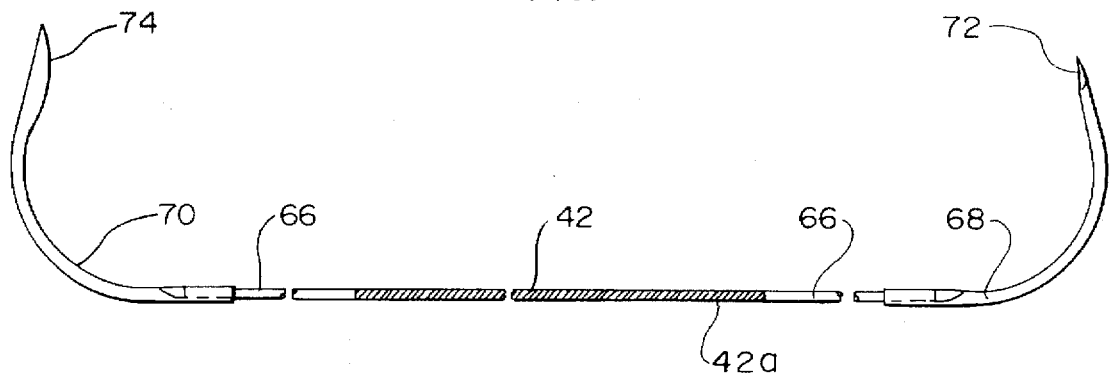
FIG. 7 is a plan view of a multistrand, surgical cable in accordance with this invention, usable with the pliers and surgical procedure shown in the previous drawings.

FIG. 7 shows the ends of cable 42, upon each of which is secured a short, wire leader section 66 to which is secured a surgical needle 68, 70. Needle 68 may define a conical, pointed tip 72 as is one conventional design, while needle 70 may define a pointed tip 74 having a cutting edge, as another conventional design. Thus, the same cable may carry two different surgical needles to facilitate the emplacement of the cable under a wider variety of situations than is available for conventional application of wire or cable windings to bones.

Also, cable 42 may have a long, multistrand portion 42a, being a wound array of preferably about 75 strands. For example, the cable configuration may comprise eight seven-strand, wound bundles which are, in turn, wrapped about a single, central bundle of 19 wound strands. The strands may be made for example of 316L ASTM F-138 Stainless Steel or titanium 6A 4V ASTM F-136 alloy. Such a cable configuration is very flexible and strong. The cable is also swaged for increased smoothness. Because of the two separate end needles, the cable can be driven by one needle through the bone, or it may be passed around the sternum as the surgeon chooses by the other needle, or both. The presence of single strand leader wire 66 on each end facilitates the passage of the cable through crimp 36, typically after cutting away the needles.

Through the use of the multistrand cable of this invention, such a cable has very good fatigue resistance and static strength, which makes it less resistance to breakage, comprising a significant improvement over corresponding monofilament wire. Also, monofilament wire cannot be tightened to the extent that cables can in the system of this invention. Often, wires break under conditions where the cable of this invention does not.

Also, the cable system of this invention can be tightened to a known tension through the use of a torque wrench, for example. This tension is thus reproducible, and can be adjusted to any desired clinical situation. Since the sternum can be more rigidly fixed, this contributes to less failure and less postoperative pain.

Also, the cable of this invention is very flexible, which makes its insertion much easier as it is wound around the sternum or other bones. This also facilitates the ease of removal of the cable if that becomes necessary. Likewise, fewer cables may be required for securing the sternum in view of the increased strength of the cables over monofilament wires, to speed up closure of the sternum.

Additionally, a cable in accordance with this invention, being stronger, can have less diameter than the wire of corresponding strength, which decreases the irritation which is common with wires. Likewise, there are no sharp ends in the implanted cable. Even if a break or failure occurs, the soft cable end is much safer than a broken wire end in terms of the risk of puncturing a blood vessel.

The above has been offered for illustrative purposes only, and is not intended to limit the scope of the invention of this application, which is as defined in the claims below.

That which is claimed is:

1. A malleable metal, tubular crimp for securing a plurality of cable sections together, said crimp defining a bore of generally oval cross-section extending entirely through said crimp to permit a plurality of said cable portions to extend therethrough in side-by-side relation, said crimp having a pair of opposed ends which each define an outwardly projecting flange.

2. The crimp of claim 1 in which each of said flanges completely surrounds said crimp.

3. A malleable metal, tubular crimp for securing a plurality of cable sections together, said crimp defining a bore of generally oval cross-section extending entirely through said crimp to permit a plurality of said cable sections to extend therethrough in side-by-side relation, said crimp having a pair of opposed ends which each define an outwardly projecting flange whereby said crimp is easily held in a pair of crimping pliers with the respective flanges being positioned laterally outside of said pliers.

4. The crimp of claim 3 in which each of said flanges completely surrounds said crimp.

5. A malleable metal tubular crimp associated with a plurality of cable sections and for securing said plurality of cable sections together, said crimp defining a bore of generally oval cross-section extending entirely through said crimp to permit a plurality of said cable sections to extend therethrough in side-by-side relation, said crimp having a pair of opposed ends which each define an outwardly protecting flange, whereby said crimp is easily held in a pair of crimping pliers with the respective flanges being positioned laterally outside of said pliers in which said bore encloses a pair of said cable sections.

6. The crimp and cable sections of claim 5 in which each of said flanges completely surrounds said crimp.

* * * * *